United States Patent [19]
Shah et al.

[11] Patent Number: 5,614,207
[45] Date of Patent: Mar. 25, 1997

[54] DRY MOUTH LOZENGE

[75] Inventors: Manoj N. Shah, Norristown; Randall G. Goodreau, Chalfont, both of Pa.

[73] Assignee: McNeil-PPC, Inc., Skillman, N.J.

[21] Appl. No.: 497,563

[22] Filed: Jun. 30, 1995

[51] Int. Cl.⁶ .................... A61K 9/20; A61K 9/68
[52] U.S. Cl. ............................ 424/440; 424/464
[58] Field of Search ................ 424/440, 195.1, 424/464

[56] References Cited

U.S. PATENT DOCUMENTS

| | | | |
|---|---|---|---|
| 3,312,594 | 4/1967 | Cyr et al. | 167/82 |
| 4,139,627 | 2/1979 | Lane et al. | 514/315 |
| 4,163,777 | 8/1979 | Mitra | 424/21 |
| 4,226,849 | 10/1980 | Schor | 424/19 |
| 4,238,510 | 12/1980 | Cherukuri et al. | 426/5 |
| 4,369,172 | 1/1983 | Schor et al. | 424/19 |
| 4,747,881 | 5/1988 | Shaw et al. | 106/209 |
| 4,753,790 | 6/1988 | Silva et al. | 424/440 |
| 4,790,991 | 12/1988 | Shaw et al. | 424/441 |
| 4,818,539 | 4/1989 | Shaw et al. | 424/441 |
| 4,843,098 | 6/1989 | Shaw et al. | 514/778 |
| 4,851,392 | 7/1989 | Shaw et al. | 514/53 |
| 4,855,143 | 8/1989 | Lowey | 424/468 |
| 4,938,963 | 7/1990 | Parnell | 424/440 |
| 4,971,798 | 11/1990 | Coia et al. | 424/440 |
| 5,055,461 | 10/1991 | Kelleher et al. | 514/162 |
| 5,059,416 | 10/1991 | Cherukuri et al. | 424/48 |
| 5,100,898 | 3/1992 | Sorrentino | 514/281 |
| 5,156,845 | 10/1992 | Grodberg | 424/440 |
| 5,196,436 | 3/1993 | Smith | 514/289 |
| 5,302,394 | 4/1994 | Beahm | 424/440 |
| 5,399,354 | 3/1995 | Ells et al. | 424/440 |
| 5,409,691 | 4/1995 | Swain | 424/49 |

FOREIGN PATENT DOCUMENTS 0451433 10/1991 European Pat. Off. .

OTHER PUBLICATIONS

Pray, W. Steven, "Dry Mouth Syndrome: Cause and Treatment," *Pharmacist*, pp. 16–24, May 1994.
*Remington's Pharmaceutical Sciences*, 18th ed., pp. 1664–1665, 1980.
"SALIX SST Lozenges," *Physicians' Desk Reference for Nonprescription Drugs*, 16th ed., pp. 797, 1995.
"SALIVART®", *Physicians' Desk Reference for Nonprescription Drugs*, 15 ed., p. 563, 1994.
"SALAGEN® Tablets", *Physicians' Desk Reference*, 49th ed., p. 1378, 1995.

*Primary Examiner*—Thurman K. Page
*Assistant Examiner*—Sharon Howard
*Attorney, Agent, or Firm*—Bernard F. Plantz

[57] ABSTRACT

The present invention relates to a dry mouth lozenge comprising a lozenge base, a demulcent, a humectant, and a pharmaceutically acceptable acidulent to stimulate the flow of saliva.

5 Claims, No Drawings

DRY MOUTH LOZENGE

FIELD OF THE INVENTION

The present invention relates to a dry mouth lozenge for stimulating the flow of saliva.

BACKGROUND OF THE INVENTION

Xerostomia, commonly known as dry mouth syndrome, is a condition in which there is a dryness of the mouth due to the lack of normal salivary secretion. As discussed by W. S. Pray, *Pharmacists*, May 1994, pp. 16–24, many oral functions may be compromised due to the lack of saliva. There may be difficulty in speaking and swallowing as well as a loss of taste. Chewing may also become difficult which may affect the nutritional condition of the patient. Drying of the mucosa may also result in mucositis, inflammation, fissuring and ulceration. Saliva is also known to provide buffering and cleansing actions, so patients suffering from xerostomia often experience decalcification of tooth surfaces as well as periodontal disease.

There are many causes of xerostomia. Salivary ducts can be obstructed or become inflamed by viral or bacterial infections. Radiation therapy to the head and neck regions can result in injury to the salivary glands. Xerostomia is often a secondary condition to other medical aliments, such as Sjogren's Syndrome, hypertension, cystic fibrosis and lupus. Xerostomia may also be induced by emotional conditions, such as fear, excitement, anxiety and other psychological problems, such as depression. Pray, supra, also reports that as many as 400 medications have been implicated in causing xerostomia. Such medications include antihypertensives, anorectics, anticonvulsants, antiparkinson agents, brochodialators, antipsychotics, antidepressants and tranquilizers.

Xerostomia is also often associated with the elderly. However, aging by itself does not appear to be a sole cause for decreased salivary flow. Rather, increased medication usage by the elderly as well as age-related medical conditions, such as Sjogren's Syndrome, hypertension, and Type II diabetes mellitus, contribute to the relationship between xerostomia and age. See Pray, supra, page 20.

Various treatments have been proposed for xerostomia. A common approach is to promote salivary flow through the use of gustatory or masticatory stimulation by chewing gum or paraffin wax. Other methods include sucking oral lozenges or hard candy.

Non-prescription saliva substitutes are also available for individuals suffering from xerostomia. Pray, supra, reports that these substitutes are more effective than plain water since they attempt to closely mimic saliva by including glycoproteins. These formulations typically contain carboxymethyl cellulose and/or mucins for lubrication and viscosity, electrolytes for buffering and remineralization, sweeteners, flavoring agents and preservatives. Salivart®, a saliva substitute marked by Gerbauer Company, is an example of a commercially available product.

U.S. Pat. No. 5,156,845 to M. G. Grodberg discusses a dry mouth lozenge for stimulating the flow of saliva. The lozenge includes a base, a sugarless sweetener, and an acidulent, such as betaine hydrochloride, and fluoride for inhibiting the erosion of tooth enamel. A sugarless chewing gum may be used as the base material.

F. W. Parnell in U.S. Pat. No. 4,938,963 describes a technique for treating xerostomia by administering a sweetened composition of Yerba Santa extract to the affected individual. The composition may be formulated as an aqueous solution, a gum or in a lozenge form. The composition may also include an agent to stimulate salivary gland secretion, such as citric acid, ascorbic acid or combinations thereof.

U.S. Pat. No. 5,409,691 to D. E. Swain proposes a saliva substitute for treating xerostomia which contains a topical solution of aluminum acetate, glycerin and a flavoring agent. This solution may further contain lemon extract or other source of citric acid for the purpose of stimulating the salivary gland secretion.

While a variety of products have been proposed for treating the conditions of xerostomia, none have achieved wide spread acceptance in the marketplace. Therefore, a need exists for a product that can be marketed without prescription for the treatment of dry mouth syndrome and that is in a lozenge form so as to avoid handling liquids, such as the commercially available saliva substitutes.

SUMMARY OF THE INVENTION

The present invention provides a dry mouth lozenge suitable for use in the treatment of xerostomia. The lozenge contains a lozenge base, a demulcent, a humectant and a pharmaceutically acceptable acidulent to stimulate the flow of saliva. The demulcent that is present in this lozenge becomes hydrated in the presence of saliva and takes on a wet, slippery texture which provides good mouth feel to patients experiencing dry mouth. The lozenge may optionally contain a pharmaceutically active ingredient for medicating the oral mucosa.

DETAILED DESCRIPTION OF PREFERRED EMBODIMENTS

The present invention provides a lozenge suitable for treatment of the symptoms of xerostomia. The lozenge contains a lozenge base, a demulcent, a humectant and a pharmaceutically acceptable acidulent to stimulate the flow of saliva. When this lozenge is sucked in the mouth, salivary flow is stimulated and the demulcent is hydrated so as to provide a wet, slippery mouth feel that alleviates dry mouth. Since the lozenge contains a base that dissolves slowly in the mouth, it provides long lasting relief to dry mouth. Dosing of the product by the patient is more convenient than the commercially available saliva substitutes which require the handling of liquids.

The lozenge may contain a hard candy base or may be a compressed tablet lozenge employing sugars as the base. These lozenge base materials, and their methods of preparation, are described in Liberman et al., *Pharmaceutical Dosage Forms: Tablets*, 2 Ed., Marcel Dekker, Inc. New York, Vol. 1, Chpt. 9, pp. 419–562 (1989), which is hereby incorporated by reference. The dry mouth lozenge will generally comprise from about 60 to about 99, preferably from about 75 to about 95, percent by weight of the base.

The hard candy lozenge base is preferably a mixture of sugar and other carbohydrates that are maintained in an amorphous or glassy condition. Suitable base materials include mixtures of corn syrup and sugar syrup. Non-cariogenic sweeteners, such as sorbitol, mannitol and hydrogenated glucose syrup, such as LYCASIN® available from Roquette America, Inc. may also be used as the hard candy base. Suitable bases for compressed tablet lozenges include sucrose and dextrose- or sucrose-modified materials, such as EMDEX® (maltose-dextrose spheres containing 92% dextrose, 2–5% maltose, and a portion of higher glucose saccharides) available from E. Mendell Co, N.Y. If a wet granulation step is used, the base for the compressed tablet lozenge may also contain a binder, such as gelatin or polyvinylpyrrolidone.

The corn syrup and sugar syrup used for the hard candy base are generally well known in the art. The ratio of corn syrup to sugar syrup is generally in the range of about 35:65 to about 50:50 (by weight dry), but other ratios may be employed to achieve the desired physical characteristics. The sugar syrup may be formed in situ or may be purchased commercially in a solution of approximately 67% by weight sugar (commonly referred to as No. 2 sugar syrup). The corn syrup that is utilized affects the sweetness and sugar grain size of the resulting lozenges. Suitable corn syrups include low conversion corn syrup (dextrose equivalent (DE) of 20–38), regular conversion corn syrup (DE of 38–48) and intermediate conversion corn syrup (DE of 48–58). For the present invention, a corn syrup with a DE of about 42 is preferred.

The demulcent used in the dry mouth lozenge of the present invention is a material that upon hydration by the saliva imparts a wet, slippery mouth feel. The demulcent also helps to alleviate irritation of the mucous membrane and prevent drying. Suitable demulcents includes methycellulose, hydroxypropyl methyl cellulose, hydroxyethyl cellulose, hydroxypropyl cellulose, carboxymethyl cellulose and mixtures thereof. Other suitable demulcents are disclosed in *Remington's Pharmaceutical Sciences*, 18th Edition, Mack Publishing Co. Inc., Easton, Pa., pp. 759–760 (1990), which is hereby incorporated by reference. The demulcent is present in the lozenge in an amount ranging from about 0.05 to about 15, preferably from about 0.2 to about 8, percent by weight of the lozenge.

To further enhance the moisturizing properties of the lozenge, a humectant, such as glycerin, propylene glycol, sorbitol and mixtures thereof, is employed in the present invention. Generally, the dry mouth lozenge will contain from about 1 to about 7.5, preferably from about 1.5 to about 5, percent by weight of the humectant.

In order to enhance the flow of saliva, an acidulent is employed in the dry mouth lozenge. Suitable acidulents include tartaric acid, citric acid, fumaric acid, malic acid, ascorbic acid, phosphoric acid and mixtures thereof. These acidulents are generally present in amounts ranging from about 0.05 to about 1, preferably about 0.1 to about 0.5, percent by weight of the lozenge.

If it is desirable to provide for a medicated lozenge, a pharmaceutically active ingredient may be employed in the present invention. Suitable medicaments which may be used include anesthetics, such as dyclonine, hexylresorcinol, menthol, phenol, eucalyptus oil, menthol eucalyptus; vitamins, such as ascorbic acid; cough suppressants, such as dextromethorphan; pharmaceutically acceptable salts thereof; and mixtures thereof. A preferred anesthetic is dyclonine hydrochloride. These medicaments are generally provided in amounts effective to provide a therapeutic dosage in a lozenge form. Suitable dosage ranges may be found in *Remington's Pharmaceutical Sciences*, 18th Ed. supra, which is hereby incorporated by reference, Liberman et at., supra. and OTC (Over-The-Counter) Monographs. Generally, the dry mouth lozenge will contain from about 0.05 to about 10 weight percent of the pharmaceutical active.

When dyclonine HCl is used as an anesthetic in the lozenge, a sufficient amount of a pharmaceutically acceptable acid, such as citric acid, is added to stabilize the dyclonine in the candy base. See U.S. Pat. No. 4,139,627 to P. A. Lane, which is hereby incorporated by reference.

Suitable auxiliary ingredients, such as natural and artificial flavors and dyes or coloring agents may also be added to the lozenge of the present invention. These auxiliary agents are added in amounts to achieve the desired product characteristics.

The dry mouth lozenge of the present invention is prepared using conventional lozenge manufacturing processes. Such processes are disclosed in Liberman et al., supra. For a hard candy lozenge, the demulcent, which has been previously dispersed in the humectant, is hydrated in water, and then mixed with the hard candy base. The resulting mixture is then cooked at about 130°–155° C. to remove excess water. Alternatively, the demulcent may be hydrated without the humectant or mixed with the hard candy base while it is being cooked. The active ingredient(s), acidulent(s), color(s), and flavor(s) are then added to the hot cooked mass and mixed. The resulting molten candy mass is then formed into the desired size and shape prior to cooling.

The compressed tablet lozenge of the present invention is formed using conventional wet granulation or direct compression techniques. The base is blended with the demulcent, humectant, acidulent and, optionally, the active ingredient, lubricated and compressed into tablets of the desired size and shape.

Specific embodiments of the present invention are illustrated by way of the following examples. This invention is not confined to the specific limitations set forth in these examples, but rather to the scope of the appending claims.

Unless otherwise stated, the percentages given below are by weight of the total lozenge weight.

EXAMPLE I

This Example discloses a medicated, dry mouth lozenge containing dyclonine HCl at 2 mg per lozenge dose. The ingredients contained in the lozenge are as follows:

| Ingredients | % Dry Wt./2.5 g Lozenge |
|---|---|
| Corn Syrup 42 DE | 38.5 |
| Sugar Syrup #2 | 57.8 |
| Carboxymethyl Cellulose | 0.5 |
| Glycerin | 2.0 |
| Dyclonine HCl | 0.08 |
| Citric Acid Anhydrous | 0.37 |
| Malic Acid | 0.37 |
| Wild Cherry Flavor | 0.35 |
| Red Color Dispersion | 0.03 |
| | 100% |

The lozenge is prepared as follows:

1. The carboxymethyl cellulose is dispersed in glycerin. The resulting dispersion is then added to a sufficient amount of water to completely hydrate the carboxymethyl cellulose.

2. The carboxymethyl cellulose solution prepared in 1. above is added to a mixture containing corn and sugar syrups in a weight ratio of 40:60. The resulting mixture is then cooked at 130°–155° C. to remove excess water.

3. The dyclonine HCl, citric and malic acids, flavor and color are added to the hot cooked mass and mixed. The resulting hot mass is then formed into 2.5 gram lozenges of the desired shape.

EXAMPLE II

This Example discloses a dry mouth lozenge having a total weight of 2.5 grams. The ingredients contained in the lozenge are as follows:

| Ingredients | % Dry Wt./2.5 g Lozenge |
| --- | --- |
| Corn Syrup 42 DE | 38.5 |
| Sugar Syrup #2 | 58.0 |
| Carboxymethyl Cellulose | 0.5 |
| Glycerin | 2.0 |
| Citric Acid Anhydrous | 0.30 |
| Malic Acid | 0.37 |
| Wild Cherry Flavor | 0.30 |
| Red Color Dispersion | 0.03 |
|  | 100% |

The lozenge is prepared as in Example II except that dyclonine HCl is not added.

EXAMPLE III

This Example discloses a dry mouth lozenge having a total weight of 2.5 grams. The ingredients contained in the lozenge are as follows:

| Ingredients | % Dry Wt./2.5 g Lozenge |
| --- | --- |
| Hydrogenated Glucose Syrup | 97.14 |
| Carboxymethyl Cellulose | 1.0 |
| Glycerin | 1.5 |
| Ascorbic Acid (Vitamin C) | 0.023 |
| Sodium Ascorbate | 0.007 |
| Orange Flavor | 0.30 |
| Yellow Color Dispersion | 0.03 |
|  | 100% |

The lozenge is prepared as follows:

1. The carboxymethyl cellulose is dissolved in water. The resulting mixture is then added to glycerin.
2. The carboxymethyl cellulose solution prepared in 1. above is added to the hydrogenated glucose syrup and cooked under vacuum at 160°–180° C. to a moisture level of about 1%.
3. The ascorbic acid, sodium ascorbate, flavor and color are added to the hot cooked mass and mixed. The resulting hot mass is then formed into 2.5 gram lozenges of the desired shape.

What is claimed is:

1. A dry mouth lozenge, comprising:

about 60 to about 99 percent by weight of a hard candy base selected from the group consisting of sorbitol, mannitol, hydrogenated glucose syrup, mixtures of corn syrup and sugar syrup; and mixtures thereof;

about 0.05 to about 15 percent by weight of a demulcent selected from the group consisting of methyl cellulose, hydroxypropyl methyl cellulose, hydroxyethyl cellulose, hydroxypropyl cellulose, carboxymethyl cellulose, and mixtures thereof;

about 1 to about 7.5 percent by weight of a humectant selected from the group consisting of glycerin, propylene glycol, sorbitol and mixtures thereof; and about 0.05 to about 1 percent by weight of a pharmaceutically acceptable acidulent to stimulate salivary flow selected from the group consisting of tartaric acid, citric acid, fumaric acid, malic acid, phosphoric acid and mixtures thereof.

2. The lozenge of claim 1 further comprising about 0.05 to about 10 percent by weight of a pharmaceutically active ingredient selected from the group consisting of dyclonine HCl, menthol, phenol, eucalyptus oil, menthol eucalyptus, dextromethorphan HBr, and hexylresorcinol.

3. The lozenge of claim 1, comprising:

about 75 to about 95 percent by weight of a mixture of corn syrup and sugar syrup;

about 0.2 to about 8 percent by weight of carboxymethyl cellulose;

about 1.5 to about 5 percent by weight glycerin; and about 0.1 to about 0.5 percent by weight of a pharmaceutically acceptable acidulent to stimulate salivary flow selected from the group consisting of tartaric acid, citric acid, fumaric acid, malic acid, phosphoric acid and mixtures thereof.

4. The lozenge of claim 3 further comprising about 0.05 to about 10 percent by weight of a pharmaceutically active ingredient selected from the group consisting of dyclonine HCl, menthol, phenol, eucalyptus oil, menthol eucalyptus, dextromethorphan HBr, and hexylresorcinol.

5. A dry mouth lozenge, consisting essentially of:

a lozenge base;

a demulcent;

a humectant; and a pharmaceutically acceptable acidulent to stimulate the flow of saliva.

* * * * *